United States Patent [19]

Hammerschmidt et al.

[11] Patent Number: 4,705,652

[45] Date of Patent: Nov. 10, 1987

[54] TETRA-ALKALI METAL SALTS OF CHROMOTROPIC ACID, A PROCESS FOR THEIR ISOLATION AND THEIR USE

[75] Inventors: Erich Hammerschmidt, Bergisch Gladbach; Horst Behre; Heinz U. Blank, both of Odenthal; Dietmar Mayer, Bergisch Gladbach, all of Fed. Rep. of Germany

[73] Assignee: Bayer Aktiengesellschaft, Leverkusen, Fed. Rep. of Germany

[21] Appl. No.: 867,111

[22] Filed: May 23, 1986

Related U.S. Application Data

[60] Division of Ser. No. 797,586, Nov. 13, 1985, abandoned, which is a continuation of Ser. No. 627,944, Jul. 5, 1984, abandoned.

[30] Foreign Application Priority Data

Jul. 28, 1983 [DE] Fed. Rep. of Germany ....... 3327275

[51] Int. Cl.$^4$ ............................................ C07C 143/30
[52] U.S. Cl. ................................................ 260/512 C
[58] Field of Search ....................... 260/512 C, 512 R

[56] References Cited

PUBLICATIONS

Donaldson, "The Chemistry and Technology of Naphthalene Compounds", Edward Arnold (publishers) Ltd., London, 1958, pp. 298–299.

*Primary Examiner*—Nicky Chan
*Attorney, Agent, or Firm*—Sprung Horn Kramer & Woods

[57] ABSTRACT

Solid crystalline tetra-alkali metal salts of chromotropic acid, a process for their isolation and their use for the preparation of pure chromotropic acid or di-alkali metal salts of chromotropic acid.

6 Claims, No Drawings

TETRA-ALKALI METAL SALTS OF CHROMOTROPIC ACID, A PROCESS FOR THEIR ISOLATION AND THEIR USE

This is a division of application Ser. No. 797,586, filed Nov. 13, 1985, now abandoned, which is a continuation of Ser. No. 627,944 filed July 5, 1984, now abandoned.

The invention relates to crystalline tetra-alkali metal salts of chromotropic acid, a process for their isolation and their use for the preparation of pure chromotropic acid (1,8-dihydroxy-naphthalene-3,6-disulphonic acid) in the form of its di-alkali metal salts.

Chromotropic acid is an important intermediate for the preparation of dyestuffs (see Ullmann's Enzyklopädie der Technischen Chemie (Ullmann's Encyclopaedia of Industrial Chemistry), 4th edition, Volume 17, page 97).

Chromotropic acid and its di-alkali metal salts have hitherto been prepared by two different processes (see Ullmann's Enzyklopädie (Ullmann's Encylopaedia) loc. cit.). In process (1), T-acid (1-amino-naphthalene-3,6,8-trisulphonic acid) is converted into chromotropic acid by alkaline pressure hydrolysis with aqueous sodium hydroxide solution. In process (2), T-acid is first converted into 1-naphthol-3,6,8-trisulphonic acid by acid pressure hydrolysis with dilute sulphuric acid, and this product is reacted with concentrated sodium hydroxide solution to give chromotropic acid in a second reaction step. In both processes, the chromotropic acid is usually isolated in the form of its disodium salt by acidification of the alkaline reaction mixtures and salting out with sodium chloride.

The two processes give chromotropic acid of varying quality (purity). A measure of the quality of the chromotropic acid is its content of diazotisable compounds; the lower this content, the better the quality of the chromotropic acid. A chromotropic acid of inferior quality (chromotropic acid C) is obtained according to process (1); its content of diazotisable compounds is greater than 6 mol %. A chromotropic acid of higher quality (chromotropic acid 4G) is obtained according to process (2); its content of diazotisable compounds is at most 3 mol %. Process (2) would thus be the more advantageous process in respect of the purity of the chromotropic acid obtained. However, process (2) has the disadvantage that, as a two-stage process, it is more complicated and expensive and requires a longer reaction time, and that considerable corrosion problems occur in the acid pressure hydrolysis.

It has now been found, surprisingly, that a qualitatively high-grade chromotropic acid (chromotropic acid 4G) can also be obtained by process (1) if the chromotropic acid obtained according to process (1) is not isolated as a di-alkali metal salt, as hitherto, but is first isolated as a tetra-alkali metal salt and this salt is converted into the di-alkali metal salt by acidification.

The tetra-alkali metal salts of chromotropic acid have not as yet been obtained in solid crystalline form and were regarded as impossible to isolate (see the corresponding statements in German Patent Specification No. 67,563, page 5, left-hand column). Surprisingly, it has been found that these tetra-alkali metal salts of chromotropic acid can certainly be isolated in solid crystalline form if certain conditions are maintained, that the tetra-alkali metal salts of chromotropic acid even crystallise in coarse crystals which can easily be separated off, and that, surprisingly, on precipitation, the tetra-alkali metal salts entrain a very much smaller amount of the impurities which always accompany chromotropic acid (aminonaphthalene- and amino-hydroxy-naphthalene-mono-, -di- or -tri-sulphonic acids) and are therefore obtained in a very much purer form than the dialkali metal salts of chromotropic acid.

The invention thus relates to tetra-alkali metal salts of chromotropic acid, of the formula

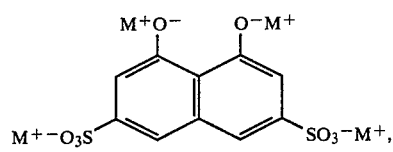

in which

M represents sodium or potassium, in solid crystalline form, a process for isolating these solid crystalline tetra-alkali metal salts of chromotropic acid and their use for the preparation of pure chromotropic acid in the form of its di-alkali metal salts.

The process for the isolation of solid crystalline tetra-alkali metal salts of chromotropic acid is characterised in that alkaline solutions of chromotropic acid are concentrated and/or saturated with corresponding alkali metal ions, and the solutions are cooled to temperatures below 70° C.

The pH value of the alkaline solutions must be at least 8.0, preferably at least 9.5.

The alkaline solutions are advantageously concentrated to chromotropic acid concentrations of 0.5 to 2.0 moles of chromotropic acid per liter of solution, preferably 0.7 to 1.5 moles of chromotropic acid per liter of solution.

For isolation, the alkaline solutions of the chromotropic acid are preferably cooled to temperatures below 30° C.

To improve the isolation yield, alkali metal ions can be added in the form of their salts, up to the saturation limit. Examples of suitable salts which may be mentioned are sodium or potassium halides, in particular the chlorides, and also the sulphates, phosphates, carbonates, nitrates, nitrites or acetates.

Examples of suitable starting materials for the isolation, according to the invention, of tetra-alkali metal salts of chromotropic acid are the alkaline solutions such as are obtained in the alkaline pressure hydrolysis of T acid (see process (1) for the preparation of chromotropic acid) or in the reaction of 1-naphthol-3,6,8-trisulphonic acid with concentrated sodium hydroxide solution under normal pressure (see process (2) for the preparation of chromotropic acid). The alkaline solutions such as are obtained when di-alkali metal salts of chromotropic acid of any desired quality are dissolved in sodium hydroxide solution can also be used.

In the use, according to the invention, of the tetra-alkali metal salts of chromotropic acid, according to the invention, for the preparation of pure chromotropic acid, the solid crystalline tetra-alkali metal salt is converted into the di-alkali metal salt of chromotropic acid by suspension in water and acidification of the suspension.

The solid crystalline tetra-alkali metal salts of chromotropic acid are also suitable as starting substances for the preparation of secondary products of chromotropic acid, such as ethyl-chromotropic acid.

EXAMPLE 1

The reaction mixture which is obtained on alkaline pressure hydrolysis (15 hours at 200° C.) of 1 mole of T-acid (disodium salt) with 1,885 g of 10% strength sodium hydroxide solution and has been freed from ammonia is concentrated to a total volume of 650 ml (content of chromotropic acid in the solution: 1.2 moles/liter) and cooled to 30° C.

The tetrasodium salt of chromotropic acid which has precipitated is filtered off with suction and washed with 250 ml of saturated sodium chloride solution.

Yield: 68% of theory of chromotropic acid, based on the T-acid used.

The tetrasodium salt is suspended in 600 ml of water and is converted into the disodium salt of chromotropic acid with 300 ml of 30% strength hydrochloric acid solution.

Yield of disodium salt: 67% of theory, based on the T-acid.

Content of diazotisable compounds: 1.8 mole %.

EXAMPLE 2

488 g of chromotropic acid C (disodium salt; content of diazotisable compounds: 11.3 mole %) are dissolved in 1,500 ml of 10% strength sodium hydroxide solution at the boiling point. 300 g of sodium chloride are added to the solution and the mixture is then cooled to 20° C. The tetrasodium salt which separates out is filtered off with suction and washed with saturated sodium chloride solution.

The tetrasodium salt is then suspended in 1,000 ml of water and converted into the disodium salt of chromotropic acid by addition of 400 ml of 30% strength aqueous hydrochloric acid.

The yield of the disodium salt of chromotropic acid is 81% of theory, based on the chromotropic acid C employed.

The content of diazotisable compounds in the purified di-alkali metal salt of chromotropic acid is only 2.3 mole %.

What is claimed is:

1. In a process for the production of chromotropic acid in which process 1-amino-naphthalene-3,6,8-trisulfonic acid is converted into chromotropic acid by alkaline pressure hydrolysis with aqueous sodium hydroxide solution and the chromotropic acid is isolated as the disodium salt, the improvement comprising
    (a) isolation of the chromotropic acid as the tetrasodium salt by concentrating the alkaline hydrolysis solution of chromotropic acid or by saturation of the said solution with sodium ion and cooling the solution to a temperature below 70° C. and
    (b) converting the tetrasodium salt into the disodium salt by acidification.
2. The process according to claim 1, wherein the pH value of the alkaline solution of chromotropic acid is at least 8.
3. The process according to claim 1, wherein the pH value of the alkaline solution of chromotropic acid is at least 9.5.
4. The process according to claim 1, wherein the alkaline solution of chromotropic acid is concentrated to a content of 0.5 to 2.0 moles of chromotropic acid per liter of solution.
5. The process according to claim 1, wherein the alkaline solution of chromotropic acid is concentrated to a content of 0.7 to 1.5 moles of chromotropic acid per liter of solution.
6. The process according to claim 1, wherein the alkaline solution is cooled to a temperature below 30° C.

* * * * *